United States Patent [19]

Loǵe et al.

[11] 4,382,790
[45] May 10, 1983

[54] DENTAL HANDPIECE

[75] Inventors: Hans Loǵe; Bernhard Kuhn, both of Biberach; Erich Bareth, Ummendorf; Gerd Löhn, Biberach, all of Fed. Rep. of Germany

[73] Assignee: Kaltenbach & Voight GmbH & Co., Biberach, Fed. Rep. of Germany

[21] Appl. No.: 186,485

[22] Filed: Sep. 12, 1980

[30] Foreign Application Priority Data

Sep. 19, 1979 [DE] Fed. Rep. of Germany ....... 2937885
Aug. 1, 1980 [DE] Fed. Rep. of Germany ....... 3029284

[51] Int. Cl.³ .............................................. A61C 1/08
[52] U.S. Cl. ................................................... 433/126
[58] Field of Search ................................ 433/127, 126

[56] References Cited

U.S. PATENT DOCUMENTS 4,211,009  8/1980  Leonard ............................. 433/126

Primary Examiner—Robert Peshock
Attorney, Agent, or Firm—Scully, Scott, Murphy & Presser

[57] ABSTRACT

A dental handpiece with a gripping sleeve-like base member which is detachably connected with a headpiece mounting a work tool, a connecting sleeve of the headpiece being insertable into the power-take off end of the base member, wherein a roll body is radially movably supported in each of one or more cutouts in the base member wall, inwardly extending therethrough with a portion of its volume, which is movable through the intermediary of a coupling element movably arranged on the base member, and which includes an inclined plane for the engagement with the roll body under the assumption of a clamping fit in contact against the connecting sleeve.

34 Claims, 23 Drawing Figures

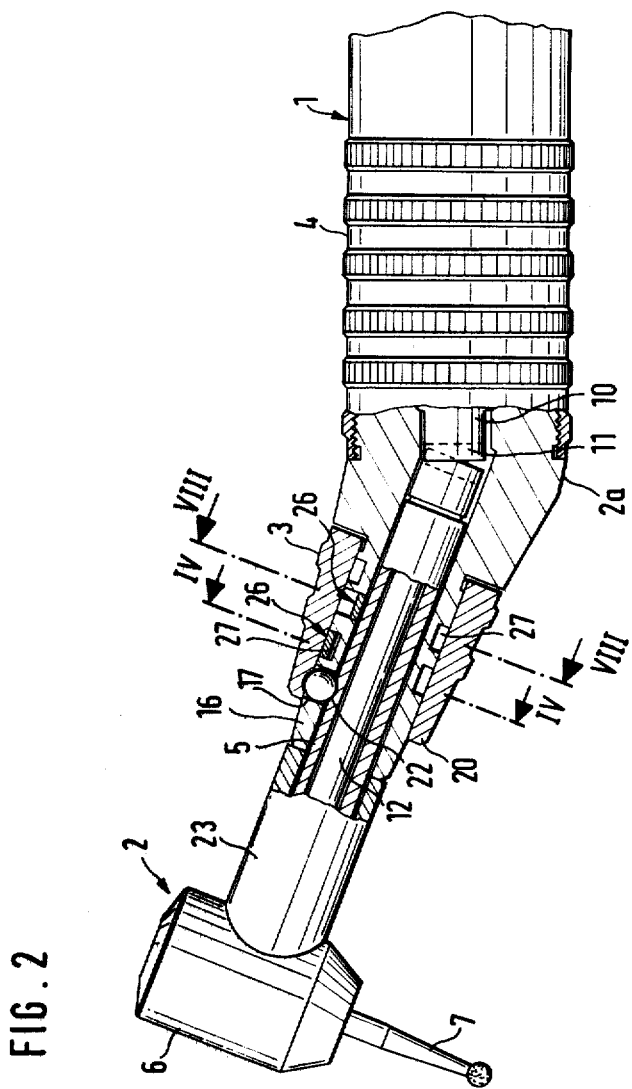

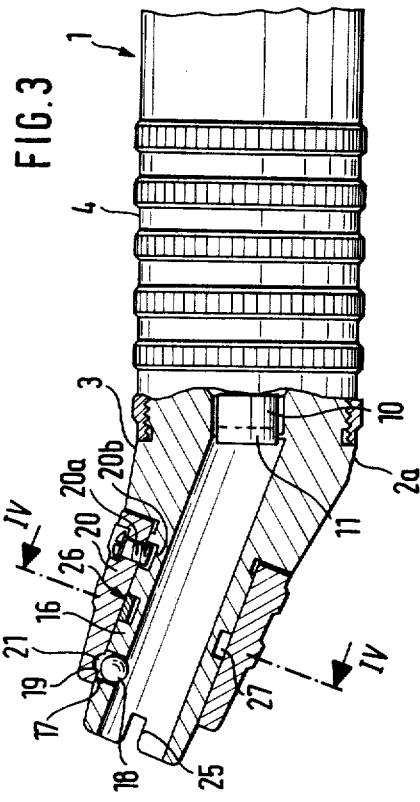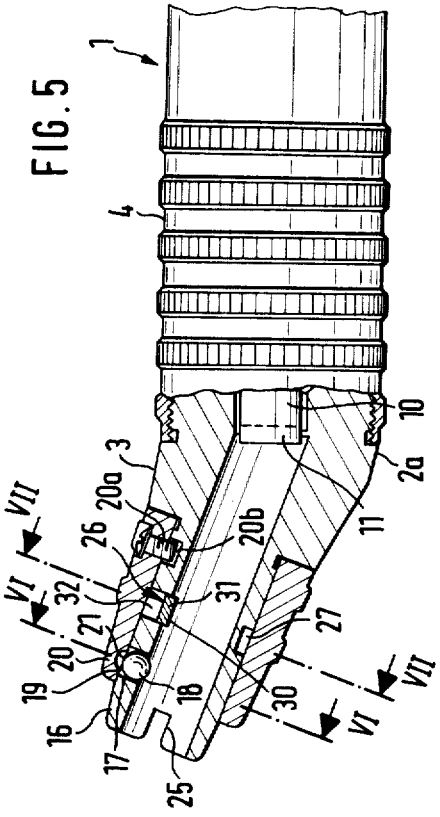
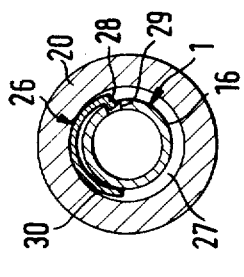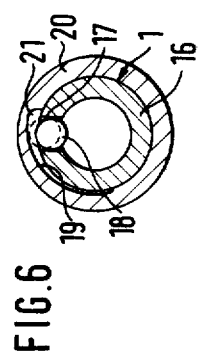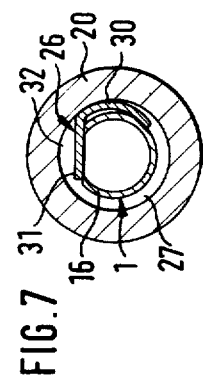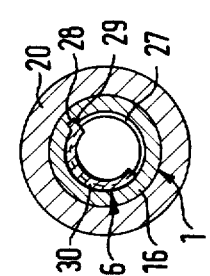

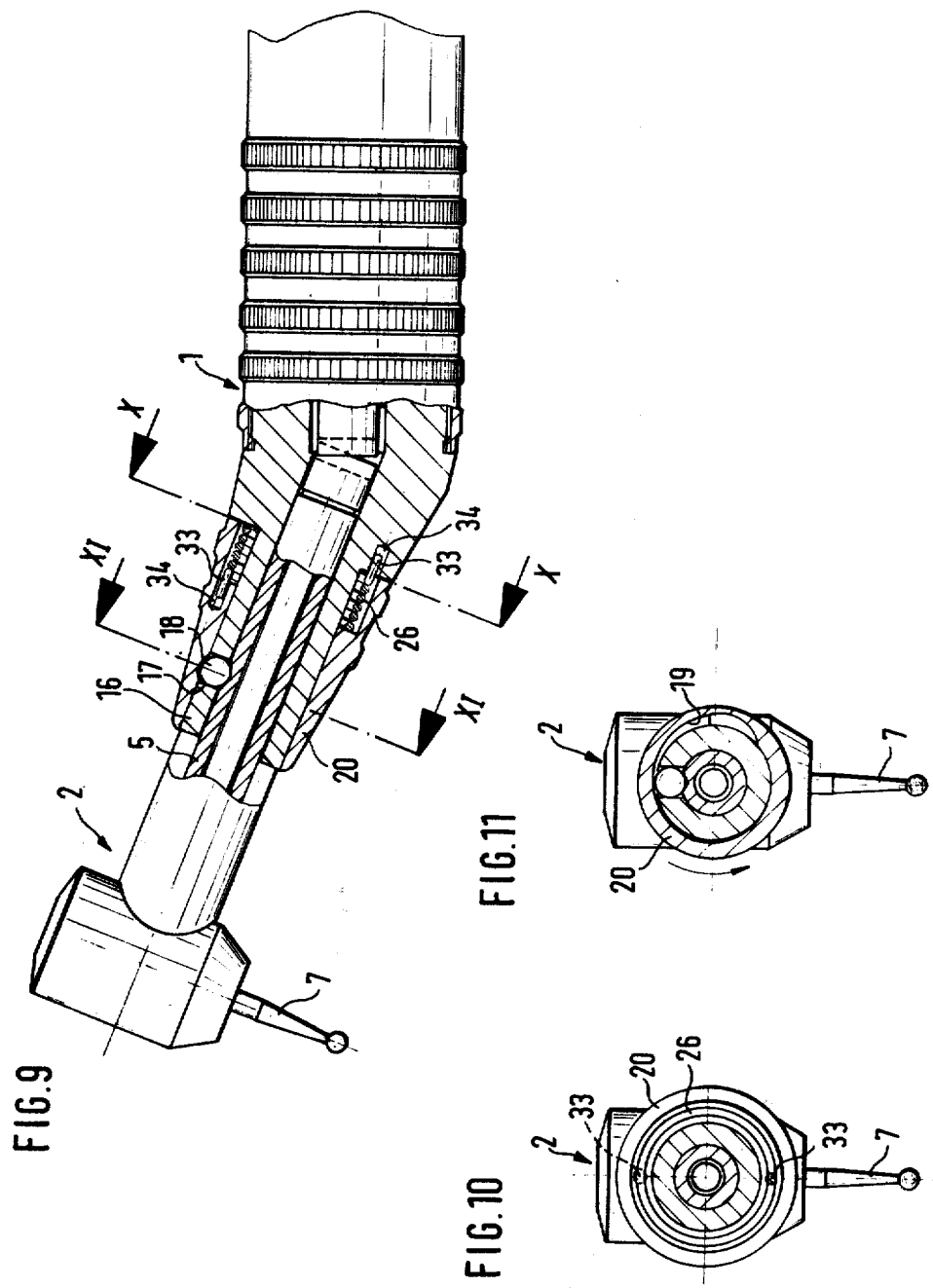

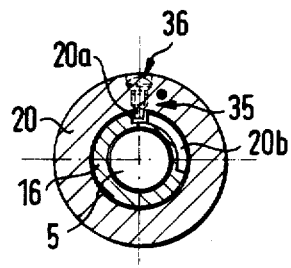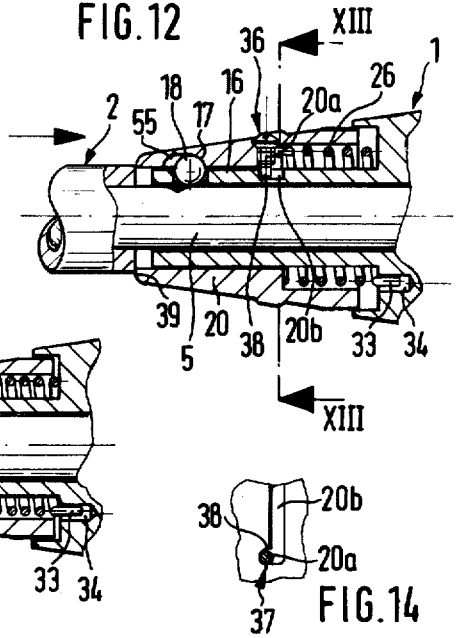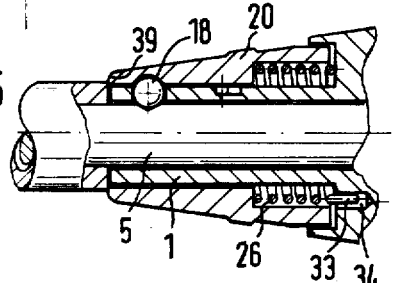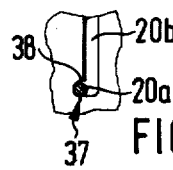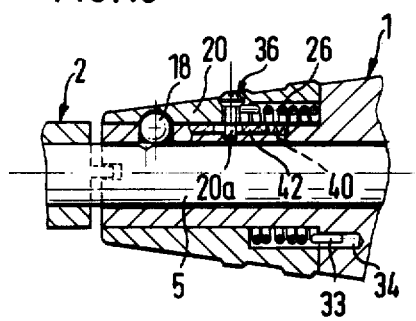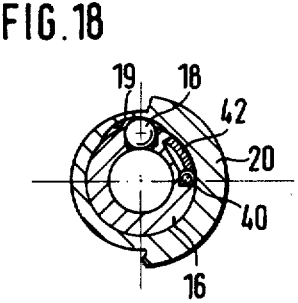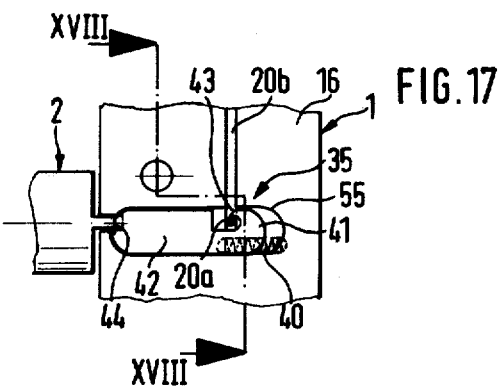

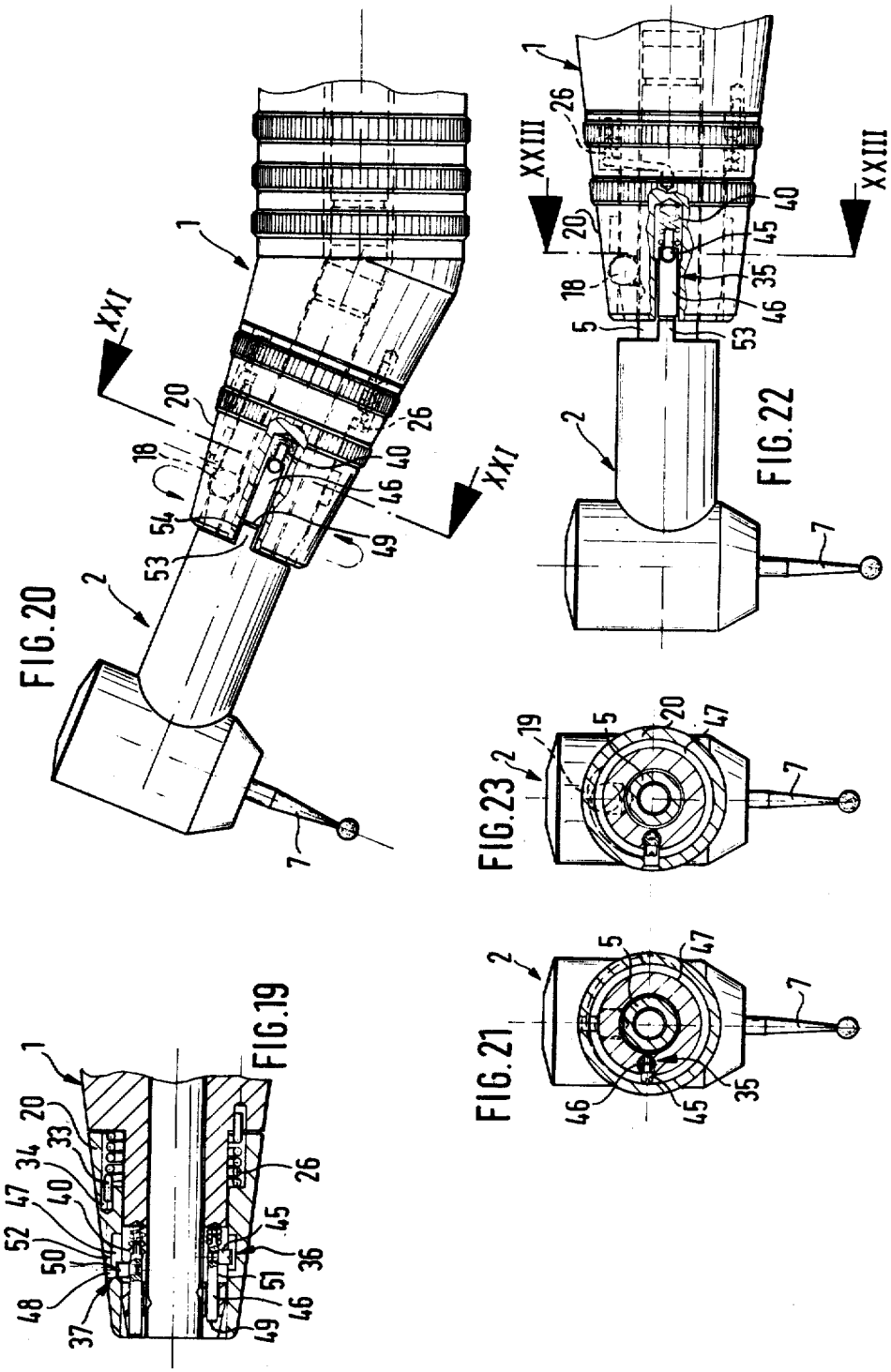

DENTAL HANDPIECE

BACKGROUND OF THE INVENTION

1. Field of the Invention

The present invention relates to a dental handpiece with a gripping sleeve-like base member which is detachably connected with a headpiece mounting a work tool, a connecting sleeve of the headpiece being insertable into the power-take off end of the base member, wherein a roll body is radially movably supported in each of one or more cutouts in the base member wall, inwardly extending therethrough with a portion of its volume, which is movable through the intermediary of a coupling element movably arranged on the base member, and which includes an inclined plane for the engagement with the roll body under the assumption of a clamping fit in contact against the connecting sleeve.

2. Discussion of the Prior Art

A handpiece of that type has become known from German Pat. No. 599,591. In this known handpiece, even when the roll body which is shaped as a ball instead of only lying against the smooth headpiece connecting sleeve engages into a recess in the headpiece connecting sleeve, it can possibly occur that, for instance due to the oscillations which take place during the operation of the handpiece, on the one hand, the roll body will release out of its clamping fit between the inclined plane which is arranged on a rotary ring forming the coupling element and, on the other hand, the smooth outer wall or the recess in the headpiece connecting sleeve. This has the consequence that the headpiece with its connecting sleeve will inadvertently slip out of the sleeve-like base member and detach from the base portion and, as a result, can cause injuries to the mouth of the patient or can even be swallowed by the patient.

SUMMARY OF THE INVENTION

Accordingly, it is an object of the present invention to provide an improved dental handpiece of the above-mentioned type which will prevent the headpiece from inadvertently detaching from the base member.

The advantages which are achieved by the present invention are essentially obtained by spring element which provides a clamping action on the portions of the handpiece which clamp to each other through the roll body, notwithstanding the shocks which are encountered during the operation of the handpiece, will prevent an unintentional movement of the roll body out of its clamping fit. Moreover, the association of the spring element with the base member, and not with the headpiece, provides the advantage that the dentist can further utilize the collective headpieces which are held in readiness without having to undertake any kind of modifications of the headpieces.

For example, for particularly robust and extreme manipulations on or with the handpiece it is, however, possible that the spring force of the spring element can be unintentionally overcome and whereupon the headpiece together with its connecting sleeve will slip out of the sleeve-like base member and detach from the base member, which can lead to injuries to the mouth of the patient.

In order to provides that even under extreme operating conditions there will be prevented an unintentional detachment of the headpiece from the base member, it is further proposed that the spring element functions with a tendency of an automatic assumption of the clamping fit of the roll body on the coupling element and on the base member.

Obtained hereby is the advantage that the coupling element is not only retained by the spring element in the position corresponding to the clamping fit of the roll body, but is also already previously moved into this position by the spring element. Thus, the dentist in order to connect the headpiece with the base member, need merely move the coupling element counter to the effect of the spring element out of the mentioned position, so that the clamping fit or action of the roll body is removed and the connecting sleeve of the headpiece can be inserted into the power-take off end of the base member. At the presently effected release of the coupling element the latter will automatically move under the effect of the spring element into the mentioned position corresponding to the clamping fit of the roll body and will be securely retained therein by the spring element whereby, even under extreme operating conditions, there will not take place any unintended detachment of the headpiece.

The present invention provides a latching device for the release of the clamping fit of the roll body opposite the effect of the spring element based upon the automatic movement of the coupling element effected into a latching position which maintains the released clamping fit, whose latched position can be practically automatically released for the purpose of assumption of a disengaged position corresponding to the clamping fit of the roll body at the insertion of the connecting sleeve of the headpiece into the drivesided end of the base member. This arrangement achieves an the additional advantage that the dentist, prior to the insertion of the connecting sleeve, need no longer slide or rotate the coupling element counter to the action of the spring element, since the latching into the position corresponding to the released clamping fit of the roll body takes place already upon the withdrawal of the previously utilized headpiece after the movement of the coupling element carried out for the release of the clamping fit.

BRIEF DESCRIPTION OF THE DRAWINGS

Advantageous embodiments of the invention may now be ascertained from the following detailed description of preferred embodiments of the invention, taken in conjunction with the accompanying drawings; in which:

FIG. 2 illustrates, partly in section, a portion of the base member with the headpiece of FIG. 1 shown detachably connected therewith;

FIG. 3 illustrates partly in section, a portion of the base member without headpiece;

FIG. 4 is a sectional view taken along line IV—IV in FIG. 3;

FIG. 5 is a modified embodiment with respect to that shown in FIG. 3;

FIG. 6 is a sectional view taken along line VI—VI in FIG. 5;

FIG. 7 is a sectional view taken along line VII—VII in FIG. 5;

FIG. 8 is a sectional view taken along line VIII—VIII in FIG. 2;

FIG. 9 illustrates, partly in section, a plan view of a dental handpiece consisting of a base member and a headpiece detachably connected therewith;

FIG. 10 is a sectional view taken along line X—X in FIG. 9;

FIG. 11 is a sectional view taken along line XI—XI in FIG. 9;

FIG. 12 shows a sectional view of a portion of the base member with a not fully inserted headpiece and with a still engaged latching arrangement;

FIG. 13 is a sectional view taken along line XIII—XIII in FIG. 12;

FIG. 14 is a developed view of the surface of the sleeve-shaped base member with a latching cutout and a therein positioned latching element pursuant to FIGS. 12 and 13;

FIG. 15 is a sectional representation pursuant to FIG. 12, however, with a fully inserted headpiece and with disengaged latching arrangement;

FIG. 16 is a representation pursuant to FIG. 12, however, with a modified latching arrangement;

FIG. 17 is a developed view of the surface of a sleeve-shaped base member with a latching cutout and a therein located latching element pursuant to FIG. 16;

FIG. 18 is a sectional view taken along line XVIII—XVIII in FIG. 17;

FIG. 19 illustrates, in section a portion of the base member with headpiece and with a modified latching arrangement with a still not fully inserted headpiece but with a still latched latching arrangement in the upper half of the drawing, and with a fully inserted headpiece with disengaged latching arrangement in the lower half of the drawing;

FIG. 20 shows a portion of the base member with headpiece pursuant to the lower half of the representation in FIG. 19 in a plan view, partly in section;

FIG. 21 is a sectional view taken along line XXI—XXI in FIG. 20;

FIG. 22 shows a plan view, partly in section, of a portion of the base member with headpiece pursuant to the upper half of the drawing in FIG. 19; and FIG. 23 is a sectional view taken along line XXIII—XXIII in FIG. 22.

DETAILED DESCRIPTION

Figure 1:
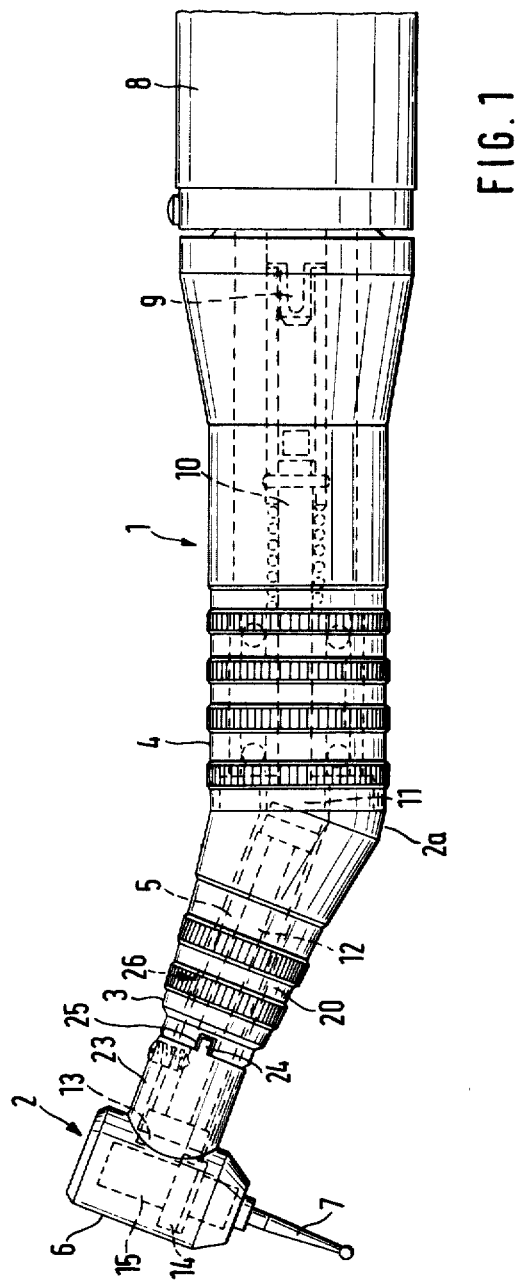
FIG. 1 illustrates a plan view of a dental handpiece consisting of a base member and a headpiece detachably connected therewith.

As may be particularly ascertained from FIG. 1 the dental handpiece, as shown in FIGS. 3 and 5, consists of a base member 1 constructed as a kind of gripping sleeve and a head piece 2 detachably connected therewith. The power-takeoff or headpiece-ended (left) section 3 of the base member 1, which in FIGS. 1, 2, 3 and 5 is shown somewhat upwardly angled at a bend location 2a, can also extend unbent, in effect, coaxial with the other (right) section 4. The headpiece 2 consists of a connecting sleeve 5 extending coaxially with the section 3, and of a head housing 6 extending at a right angle relative thereto and in which there is supported a dental treatment tool 7, for example, a rotatable drill. The head housing 6 and the connecting sleeve 5, instead of the angled arrangement, can also extend coaxially relative to each other.

The base member 1, pursuant to FIG. 1, is detachably connected at its free (right) end with a drive element 8, for instance, an electrical micromotor. Hereby, a rotary driver 9 of the drive element 8 is in engagement with a drive shaft 10 which is rotatably supported in the base member 1, which shaft ends in the region of the bend location 2a. The drive shaft 10, in turn, includes a driver 11 at its free (left) end, for example, a spur gear which stands in detachable engagement with an intermediate drive shaft 12 of the headpiece 2 supported in the connecting sleeve 5. The intermediate drive shaft 12 is, in turn, in engagement at its free (left) end with a spur gear 13 and with a gear ring 14 of a receiving sleeve 15 supported in the head housing 6 and which detachably retains the work tool 7. Basically, a turbine adapted to place the work tool 7 into rotation can also be arranged in the head housing 6 whereby the drive component 8, the drive shaft 10 and the intermediate drive shaft 12 can be eliminated and there would be provided a suitable compressed air supply for the turbine.

The detachable interconnection between the base member 1 and the headpiece 2, with the provision of an engagement between the drive shaft 10 and the intermediate drive shaft 12, is effected in a manner wherein the headpiece connecting sleeve 5 is slid into the section 3 of the base member 1 from the power-takeoff end. Arranged in a cutout 17 extending through the base member wall, is a radially moveably supported roll body 18 formed as a ball, as shown in FIG. 6, and which extends inwardly through the wall 16 with a small portion of its volume. The cutout 17 hereby narrows towards the interior of the sleeve in order to prevent the falling out of the roll body 18 when the headpiece 2 is removed. Through the intermediary of a coupling element, formed as a rotary or turn ring, which is rotatably arranged on the base member 1 and which includes an inclined plane 19 serving to press the roll body 18 against the connecting sleeve 5, the roll body 18 is movable into fixed contact against the connecting sleeve 5 so as to assume a clamping fit. The inclined plane 19 is formed by the bottom of a groove 21 which evidences a constantly changing clamping depth and which extends over a portion of the inner circumference of the coupling element 20 formed as a rotary ring. For the guidance of the rotary ring during the turning thereof, or for the axial securing of the rotary ring, the latter possesses an internal radial projection 20a in the shape of a screw or helix which engages into a peripheral groove 20b of the base member 1 extending at least over the length of the groove 21. In lieu of the form of a rotary or turn ring, the coupling element can also be constructed in the shape of a slider element, for example a pusher ring with an inclined plane arranged in a suitable manner, for example, in accordance with German Pat. No. 599,591.

For the engagement of at least one roll body 18 which is in the shape of a ball, the outside of the connecting sleeve 5 is provided with at least one recess 22 which presently is formed by a cup-like indentation. For the easy locating of this cup-like indentation during the insertion of the connecting sleeve 5 into the base member a shaft sleeve 23 which projects from the head housing 6 and which extends over the contact sleeve 5 for a portion of its length, possesses as an adjusting aid projection-shaped engaging means 24 at its end for engagement into slit-shaped complimentary engaging means 25 arranged on the headpiece end of the base member 1.

In this manner there is afforded that the angled or inclined head housing 6 will constantly assume the same angular position with regard to the base member 1. However, when as the head housing 6 is not angled with respect to the connecting sleeve 5 but extends coaxially with the sections 3 and 4 of the base member 1, at least one recess 22 can be replaced by an annularly extending groove and the engaging means as well as the counterengaging means can be eliminated.

Associated with the base member 1 is a spring member 26 which secures or reinforces the clamping fit or action of the roll body 18.

In the embodiment according to FIGS. 3 and 4 the spring member 26 is arranged between the coupling element 20 and the base member 1. The spring member 26 hereby lies against the coupling element 20 as well as against the base member 1. In this manner the coupling element and the base member are braced relative to each other under the action of the spring member. This will prevent the coupling element from being inadvertently moved with respect to the base member whereby the roll body 18 remains in its latching position and maintain its clamping action.

A similar effect is achieved when, according to FIG. 8, the spring element 26 is arranged between the headpiece connecting sleeve 5 and the base member 1 and acts on the connecting sleeve as well as on the base member. Hereby, the connecting sleee and the base members are directly clamped to each other so as to also secure the clamping fit or action of the roll body 18. This embodiment evidences a still further advantage which consists of in that even when the dentist or an assistant inadvertently causes the coupling element 20 to move up to the assumption of the clamping fit of the roll body 18, in essence, to be drawn on sufficiently secure, or even to be completely drawn on, that there will be prevented an otherwise slipping out of the headpiece 2 with its connecting sleeve 5 from the sleeve-shaped base member 1 as a result of the direct resilient clamping between the connecting sleeve and the base member.

A suitable embodiment through which these are achieved the two previously described effects is shown in FIG. 2, in which a spring member 26 is provided, respectively, between the coupling element 20 and the base member 1, as well as between the connecting sleeve 5 and the base member 1.

For the same purpose there can also be provided only a single spring member 26 which acts concurrently on the coupling element 20 and on the base member 1 and, the other hand acts as well on the connecting sleeve 5 and on the base member 1. A practical embodiment thereof is illustrated in FIG. 7.

The spring element 26 is suitably arranged in a recess 27 in the base member 1 which, pursuant to FIGS. 4, 7, 8 is constructed as an annular groove extending about the circumference of the sleeve-shaped base member 1. In the embodiment pursuant to FIGS. 4 and 7, the annular groove is arranged on the exterior, and in the embodiment pursuant to FIG. 8 in the interior of the base member 1.

For the fastening of the spring member 26, the last-mentioned is provided with an extension 28 which engages in a recess 29 in the base member 1. In the embodiment pursuant to FIG. 4, the extension 28 is angled radially inwardly, and in the embodiment pursuant to FIG. 8 radially outwardly.

The spring member 26 can be constructed as desired. Suitable is a construction as a snap ring or as a leaf spring 30. Such a leaf spring 30, as shown in the embodiments according to FIGS. 4, 7 and 8, can extend over the entire length (FIGS. 4 and 8) or over a portion of its length (FIG. 7) in the direction of the circumference of the sleeve-shaped base member 1.

Extremely suitable is the embodiment pursuant to FIG. 7 which illustrates an example for the arrangement and construction of only a single spring member 26 which concurrently exerts the above-mentioned two effects. This embodiment consists of in that recess 27 which receives the leaf spring 30 is arranged on the exterior of the base member wall 16, and in which the leaf spring, relative to the inner diameter of the base member, evidences a tangential inwardly directed radial bent position 31 which engages into a cutout 32 extending through the base member wall 16 and, in the region of this recess, tangentially contacts against the headpiece connecting sleeve 5. The cutout 32 hereby forms, to some measure, a continuation or completion of the recess 27.

The spring member 26 according to FIGS. 9 through 23 is thus constructed in a manner as to exert an effect in the context of an automatic assumption of the clamping fit of the roll body 18 on the coupling element 20 and on the base member 1. The spring member 26 is hereby constructed as a compression spring, in essence a tension spring, supported with its one end on the coupling element 20 and with its other end on the base member. As may be ascertained, the spring element is formed by a helical coil spring which encompasses the base member 1. At both of its ends this coil spring respectively includes an axially directed extension 33. The two extensions 33 are each respectively inserted into an axially oriented blind hole 34 formed in the coupling element 20 and in the base member 1.

The coupling element 20 is constructed as a rotary or turning ring which is provided on its inner circumference with the inclined plane 19. Through rotation of the coupling element 20 in the direction of the arrow shown in FIG. 3, the spring member 26 is stressed, so that due to the increased play caused by the herewith similarly moved inclined plane 19, the roll body 18 will move radilly outwardly and the connecting sleeve 5 can be pulled out. In this position, in accordance with the embodiment pursuant to FIGS. 9 through 11 the dentist must hold the coupling element 20 until there is slid in a new headpiece 2 with its connecting sleeve 5. Thereafter he can release the coupling element 20 whereupon, through the action of the spring member 26, there is again automatically produced the clamping fit of the roll body 18.

The mentioned retention and release is facilitated in the embodiments pursuant to FIGS. 12 through 23 in which a movement of the coupling element 20 for release of the clamping fit of the roll body 18 against the effect of the spring member 26 automatically effected into a latching position maintaining the released clamping fit or action is provided by a latching arrangement 35, the latching position of which, for the purpose of securing a disengaged position corresponding to the clamping fit of the roll body, upon the insertion of the connecting sleeve 5 of the headpiece into the drive end of the base member 1, can be released practically automatically. Hereby, the construction is such that the latching arrangement 35 evidences a latching element 36 which is pressed out of its latching position upon the insertion of the connecting sleeve 5 against the effect of a return spring, and which has a locking recess 37 associated therewith for the assumption of the latching position.

In the embodiment according to FIGS. 13 and 15 the spring member 26 concurrently forms a return spring. In the embodiment pursuant to FIGS. 13 and 15, as well as that pursuant to FIGS. 16 to 18, the latching element 36 is arranged on the coupling element 20 and the locking recess 37 on the base member 1. Furthermore, the latching element 26 is formed by an inwardly extending radial protuberance 20a of the coupling element 20, and the locking recess 37 through an axial bulge 38 which is provided for the engagement of the radial protuberance 20a and which is arranged to extend over a portion of the outer peripheral groove 20b of the base member 1 extending along a portion of the circumference. Hereby, the axial bulge 38 is directed towards the head-sided handpiece end.

In the embodiment according to FIGS. 13 and 15, the coupling element 20a which is provided with the latching element 36 is axially movably located on the base member 1. For this purpose the coupling element 20 is provided with at least one follower step 39 which, during the insertion of the connecting sleeve 5 serves for the contact of the headpiece 2, and which is formed herein by the left end of the coupling element 20. In this manner it is possible that upon the pressing of the headpiece 2 towards the right, in effect, in the direction of the arrow shown in FIG. 12 against the base member 1, the coupling element which is constructed as a rotary ring is axially displaced in the direction of the arrow onto the base member 1 against the pushing action of the spring member 26, until the radial protuberance 20a which is in the latching position (FIG. 14) is moved out of the axial bulge 38 into its unlatched position, whereupon the coupling element 20 which is formed as a rotary ring will, under the torsional effect of the spring element 26 as ascertained in FIG. 15, will rotate into a position corresponding to the clamping fit of the roll body 18. In order to render feasible the mentioned axial displacement, the recess 17 includes an axial widening 55. In order to release the headpiece 2, the coupling element 20 need only be turned back so far counter to the torsional effect of the spring member 26 until the radial protuberance 20a, under the pushing action of the spring member 26, which here concurrently serves as a return spring, is again moved into its latching position as shown in FIG. 14.

In the embodiments pursuant to FIGS. 16 to 18 and according to FIGS. 19 through 20, in addition to the spring member 26 there is provided a special, in essence additional return spring 40.

In the constructional embodiment pursuant to FIGS. 16 to 18, the configuration is such that the coupling element 20 which is provided with the latching element 26 is axially immovably fixed on the base member 1, and wherein the axial bulge 38 is formed through the opening of a hook-shaped end 41 pusher 42 which is axially movably supported in the ball member 1 and retained in the latching position under the effect of the return spring 40 which is specially constructed as a pressure, whose hook-shaped end 41 includes an incline 43 allowing for the sliding over of the latching element 36 taking place during the assumption of the latching position. The pusher 42 is provided with at least one follower step 44 which, during the insertion of the connecting sleeve 5, serves for the contacting of the headpiece 2, and which is herein formed by the left end of the pusher. At the pressing of the headpiece 2 towards the right against the base member 1, a nose of the headpiece 53 projects through a slot 54 provided in the base member 1 into contact against the left end of the pusher 42, whereupon the pusher is displaced towards the right against the pushing effect of the return spring 40 until the radial protuberance 20a which is in the latching position (FIG. 7) is moved out of the axial bulge 38 into its unlatched position, whereupon the coupling element 20 which is formed as a rotary ring will rotate under the torsional action of the spring member 26 into a position corresponding to the clamping fit. In order to release the headpiece 2, the coupling element 20 is rotated back so far against the torsional action of the spring member 26 until the radial protuberance 20a slides, counter the pushing effect of the return spring 40, over the inclined surface 43 of the pusher 42 and the last mentioned will hereby move towards the right into a guide groove 56 of the base member 1 until the radial protuberance 20a is finally latched into the axial bulge 38 and the pusher 42, under the effect of the return spring 40, will assume its position as shown in FIG. 17.

In the embodiment pursuant to FIGS. 19 to 23 the construction is such that the coupling element 20, which is provided with the latching element 36, is arranged axially immovably on the base member 1 and the latching element 36 is arranged on the base member 1 and the locking recess 37 on the coupling element 20. From FIGS. 19 through 23 there can be ascertained that the latching element 36 is formed by an outwardly projecting radial protuberance 45 of a pusher 46 supported axially movably in the base member 1 and retained in the latching position under the effect of the special return spring 40, and whrein the locking recess 37 is formed by an axial bulge 48 arranged at one end of an inner circumferential groove 47 of the coupling element 20 and extending over a portion of the circumference, and being provided for the engagement of the radial protuberance 45. Hereby, the foregoing relates to the construction of the latching arrangement 35 as a reversal of the construction pursuant to FIGS. 12 through 18. However, according to FIGS. 19 through 23, the axial bulge 48 is again directed towards the head-sided handpiece end. As the drawing further illustrates, the pusher 46 is constructed as a push rod whose head end is constructed as a follower stop 49 serves, during the insertion of the connecting sleeve 5, for the contacting of the headpiece 2.

At the pressing of the headpiece 2 towards the right against the base member 1, the headpiece nose 53 extends through the slot 54 provided in the base member 1 into contact with the left end of the pusher 46 whereby the last-mentioned is displaced against the pushing effect of the return spring 40 until the radial protuberance 45 found in the latching position (FIG. 19 upper, as well as FIGS. 22 and 23) is moved out of the axial bulge 48 into its unlatched position, whereupon the coupling element 20 which is constructed as a rotary ring will, under the torsional action of the spring element 26 rotate into a position corresponding to the clamping fit of the roll body 18 (FIG. 19, lower as well as FIGS. 20 and 21). In order to release the headpiece 2, the coupling element 20 is rotated back so far until the radial protuberance 45 will, under the effect of the return spring 40, latch into the axial bulge 48 and will again assume the position as shown, for example, in the upper part of FIG. 19.

In the embodiment pursuant to FIGS. 19 through 23 the latched position and unlatched position of the latching arrangement 35 are represented by identifying markings 50, 51. These markings can also be provided in the embodiment of FIGS. 12 through 18. FIGS. 19 through 23 show that the marking 50 for the latched position is formed by the outer end of the outwardly projecting radial protuberance 45, and the marking 51 for the unlatched position by the bottom of the axial bulge 48 or by the pusher 46, and that above the bulge 48 in the coupling element 20 there is provided an opening 52 forming a viewing window. The markings 50, 51 can, for example, evidence different colorations.

What is claimed is:

1. Dental headpiece comprising a gripping sleeve-like circular base member; a headpiece having a work tool supported thereon detachably connected to said sleeve-like base member; said headpiece having a connecting sleeve insertable into a bore in an end of said base member; said base member having at least one cutout therein in its circular sleeve wall; a roll body being radially movably supported in each of said cutouts so as to have a portion of the volume of the roll body extending inwardly therethrough; a sleeve-like coupling element surrounding said base member and being movably arranged relative to said base member, said coupling element including an inclined cam surface for engaging said roll body and radially moving said roll body, when said coupling element is moved relative to said base member, to cause said roll body to assume a clamping fit in contact against said connecting sleeve; and a separate spring means for resiliently bearing between said base member and said connecting sleeve for securing a clamping fit of said roll body to prevent inadvertent loosening of said roll body relative to said connecting sleeve of the headpiece.

2. Dental headpiece comprising a gripping sleeve-like circular base member; a headpiece having a work tool supported thereon detachably connected to said sleeve-like base member; said headpiece having a connecting sleeve insertable into a bore in an end of said base member; said base member having at least one cutout therein in its circular sleeve wall; a roll body being radially movably supported in each of said cutouts so as to have a portion of the volume of the roll body extending inwardly therethrough; a sleeve-like coupling element surrounding said base member and being movably arranged relative to said base member, said coupling element including an inclined cam surface for engaging said roll body and radially moving said roll body, when said coupling element is moved relative to said base member, to cause said roll body to assume a clamping fit in contact against said connecting sleeve; and a separate spring means for resiliently bearing between said base member and said coupling element for securing a clamping fit of said roll body to prevent inadvertent loosening of said roll body relative to said connecting sleeve of the headpiece.

3. Dental handpiece as claimed in claim 1 or 2, said spring means being arranged intermediate said coupling element and said base member and acting on said coupling element and on said base member.

4. Dental handpiece as claimed in claim 1 or 2, said spring means being arranged intermediate said connecting sleeve and said base member and acting on said connecting sleeve and said base member.

5. Dental handpiece as claimed in claim 1 or 2, said spring means comprising a single spring element.

6. Dental handpiece as claimed in claim 1 or 2, comprising a recess in said base member, said spring means being arranged in said recess.

7. Dental handpiece as claimed in claim 1 or 2, said spring means including an extension; said base member having a recess formed therein adapted to be engaged by said extention.

8. Dental handpiece as claimed in claim 1 or 2, said spring means comprising a snap ring.

9. Dental handpiece as claimed in claim 1 or 2, said spring means comprising a leaf spring.

10. Dental handpiece as claimed in claim 9, said leaf spring extending essentially in the direction of the circumference of said base member.

11. Dental handpiece as claimed in claim 9, comprising a recess in the exterior of the base member wall for receiving said leaf spring; said leaf spring including a tangential bent portion directed radially inwardly relative to the inner diameter of said base member; a cutout in said base member wall, said bent portion extending through said cutout and tangentially contacting said connecting sleeve in the region of said cutout.

12. Dental handpiece as claimed in claim 1 or 2, said spring means acting on said coupling element and on said base member to effect the automatic assumption of the clamping fit by said roll body means.

13. Dental handpiece as claimed in claim 12, said spring means comprising a compression spring having one end supported on said coupling element and the other end supported on said base member.

14. Dental handpiece as claimed in claim 13, said spring means comprising a tension spring; said coupling element being a rotary ring having said inclined surface at the inner circumference thereof.

15. Dental handpiece as claimed in claim 14, said tension spring being a helical coil spring encompassing said base member.

16. Dental handpiece as claimed in claim 15, said helical coil spring including an axially directed extension at both ends thereof, said extensions being respectively inserted in axially directed blind holes formed in said coupling element and in said base member.

17. Dental handpiece as claimed in claim 12, comprising latching means for automatically moving into a position maintaining the latching at release of said clamping fit responsive to movement of said coupling element counter to the effect of said spring means for release of the clamping fit of said roll body means, said latching position being releaseable for the assumption of an unlatched position corresponding to the clamping fit of said roll body means upon insertion of said connecting sleeve into the drive end of said base member.

18. Dental handpiece as claimed in claim 17, said latching means comprising a latching element adapted to be pressed out of the latching position counter to the effect of a return spring upon insertion of said connecting sleeve; and a locking recess being associated with said latching element for the assumption of said locking position.

19. Dental handpiece as claimed in claim 18, said return spring being formed by said spring means.

20. Dental handpiece as claimed in claim 18, said latching element being located on said coupling element and said locking recess being located on said base member.

21. Dental handpiece as claimed in claim 20, said latching element being formed by an inwardly extending radial protuberance of said coupling element, and said locking recess being formed by an axial bulge at one end of an external groove extending over a portion of the circumference of the base member and provided for engagement by said latching protuberance.

22. Dental handpiece as claimed in claim 21, said axial bulge being directed towards the head end of said handpiece.

23. Dental handpiece as claimed in claim 21, said coupling element with said latching element being axially movably arranged on said base member.

24. Dental handpiece as claimed in claim 23, said coupling element including at least one follower stop for contacting said headpiece during insertion of the connecting sleeve.

25. Dental handpiece as claimed in claim 18, comprising a separate return spring in addition to said spring means.

26. Dental handpiece as claimed in claim 21, said coupling element with said latching element being axially immovably arranged on said base member, said axial bulge being formed through the opening of a hook-shaped end of pusher means axially movably supported in said base member and retained in the latching position under the effect of said return spring, said hook-shaped end having an incline facilitating sliding thereover of said latching element during the assumption of the latching position.

27. Dental handpiece as claimed in claim 26, said pusher means including at least one follower stop for contacting the headpiece during the insertion of said connecting sleeve.

28. Dental handpiece as claimed in claim 18, said coupling element with said latching element being axially fixed on said base member, said latching element being located on said base member and said locking recess on said coupling element.

29. Dental handpiece as claimed in claim 28, said latching element being formed by an outwardly projecting radial protuberance of a pusher means which is axially movably supported in said base member and retained in the latching position under the effect of the return spring, and said locking recess is formed by an axial bulge at one end of an inner circumferential groove in said coupling element and extending over a portion of the circumference thereof and provided for the engagement of the radial protuberance.

30. Dental handpiece as claimed in claim 29, said axial bulge being directed towards the headpiece end of said handpiece.

31. Dental handpiece as claimed in claim 29, said pusher means comprising a pusher rod, the headpiece-sided end of said pusher rod being a follow stop for contacting said headpiece during the insertion of said connecting sleeve.

32. Dental handpiece as claimed in claim 17, comprising markings for identifying the latching and unlatching positions of said latching means.

33. Dental handpiece as claimed in claim 32, said marking for the latching position being formed through the outer end of the outwardly projecting radial protuberance and the marking for the unlatched position by the bottom of the axial bulge; and an opening forming a viewing window being provided in said coupling element above said bulge.

34. Dental handpiece as claimed in claim 32, said markings having different colorations.

* * * * *